(12) United States Patent
Coggins et al.

(10) Patent No.: US 10,062,228 B2
(45) Date of Patent: Aug. 28, 2018

(54) PERSON IDENTIFICATION SYSTEM

(71) Applicant: G4S MONITORING TECHNOLOGIES LIMITED, Leicester (GB)

(72) Inventors: Tom Coggins, Leicester (GB); John Potter, Leicester (GB)

(73) Assignee: G4S MONITORING TECHNOLOGIES LIMITED, Leicester (GB)

( * ) Notice: Subject to any disclaimer, the term of this patent is extended or adjusted under 35 U.S.C. 154(b) by 0 days.

(21) Appl. No.: 14/889,683

(22) PCT Filed: May 9, 2014

(86) PCT No.: PCT/GB2014/051430
§ 371 (c)(1),
(2) Date: Nov. 6, 2015

(87) PCT Pub. No.: WO2014/181126
PCT Pub. Date: Nov. 13, 2014

(65) Prior Publication Data
US 2016/0125678 A1    May 5, 2016

(30) Foreign Application Priority Data
May 10, 2013  (GB) .................................. 1308419.9

(51) Int. Cl.
*C07C 9/00* (2006.01)
*A61B 5/00* (2006.01)
(Continued)

(52) U.S. Cl.
CPC .......... *G07C 9/00111* (2013.01); *A61B 5/082* (2013.01); *A61B 5/4845* (2013.01);
(Continued)

(58) Field of Classification Search
None
See application file for complete search history.

(56) References Cited

U.S. PATENT DOCUMENTS 4,952,913 A    8/1990  Pauley et al.
5,811,897 A *  9/1998  Spaude ............... B60R 25/2027
                                              307/149
(Continued)

FOREIGN PATENT DOCUMENTS

EP    0109184 A2    5/1984
EP    0843425 A2    5/1998
(Continued)

OTHER PUBLICATIONS

Combined Search and Examination Report, dated Nov. 18, 2013, GB1308419.9, 2 pages.
(Continued)

*Primary Examiner* — Daniel L Negron

(57) ABSTRACT

A person identification device 100 has a tag 110 with a code and a tamper evident tether 120 able to secure the tag 110 to a person having a body. The person identification device also has a signal generator 140 able to generate a signal representing the code. The tag 110 has a capacitive contact 130 able to capacitively couple the signal into the body of the person.

9 Claims, 7 Drawing Sheets

(51) Int. Cl.
*A61B 5/08* (2006.01)
*G07C 9/00* (2006.01)
*G08B 25/01* (2006.01)
*G08B 21/04* (2006.01)

(52) U.S. Cl.
CPC ........ *G07C 9/00087* (2013.01); *A61B 5/0028* (2013.01); *A61B 5/6801* (2013.01); *G07C 2009/00619* (2013.01); *G07C 2009/00809* (2013.01); *G08B 21/0446* (2013.01); *G08B 21/0453* (2013.01); *G08B 25/016* (2013.01)

(56) References Cited

U.S. PATENT DOCUMENTS

| | | | |
|---|---|---|---|
| 6,422,911 | B1 | 7/2002 | Grzesek |
| 8,308,640 | B2* | 11/2012 | Baldus .................. G06F 19/323 340/539.12 |
| 2002/0084904 | A1 | 7/2002 | De La Huerga |
| 2003/0173408 | A1 | 9/2003 | Mosher |
| 2010/0263031 | A1* | 10/2010 | Tsuchiya ................ G06F 21/32 726/7 |
| 2014/0273829 | A1* | 9/2014 | Chandra .............. H04B 13/005 455/41.1 |

FOREIGN PATENT DOCUMENTS

| | | |
|---|---|---|
| WO | WO 2006/054211 A1 | 5/2006 |
| WO | WO-2006064397 A2 | 6/2006 |

OTHER PUBLICATIONS

International Search Report, dated Jul. 16, 2014, 4 pages; European Patent Office, International Searching Authority.

* cited by examiner

PERSON IDENTIFICATION SYSTEM

CROSS REFERENCE TO RELATED APPLICATIONS

The present application is a U.S. National Stage patent application of International Patent Application No. PCT/GB2014/051430, filed on 9 May 2014, which claims priority from Great Britain Patent Application No. 1308419.9 filed 10 May 2013, the priority and benefit of which are claimed and the disclosures of which are incorporated herein by reference in their entirety.

The invention relates to a person identification system. More specifically, but not exclusively, the invention relates to identifying a person whose behaviour is being monitored and optionally controlled.

Various techniques are known for remotely identifying a person, for example, the identity of a person may be verified by the use of a secret question or a pin code. However, these methods have the drawback that the secret question or pin code can become known or deliberately given to, and used by, an unauthorised person to circumvent behavioural control. Other methods include voice verification, facial recognition, or fingerprint recognition. However, these techniques can be unreliable, for example, facial recognition may fail if the person is wearing a hat or glasses. In other techniques, images may be monitored by a human operator, however, this technique is slow and prone to human error.

Hence, it would be advantageous to be able to reliably and efficiently confirm the identity of a person in a manner than is less easily circumvented.

The invention utilizes a signal transmitted through the human body of a person to allow recognition and identification of the person, which is more reliable than measuring physical features of the person, for example, with this system, it would be impossible for identical twins to be mixed up despite them having identical physical features, as the signal transmitted through the body identifies the particular twin.

According to a first aspect of the invention, there is provided a person identification device. The person identification device comprises a tag having a code. A tamper evident tether is able to secure the tag to a person having a body. A signal generator is able to generate a signal representing the code. The tag has a capacitive contact able to capacitively couple the signal into the body of the person. The fact that the signal representing the code is capacitively coupled to the body means that the signal, and therefore the code, may be detected all over the body of the person, for example, the code may be detected at a monitoring unit or detector the person is touching. The code uniquely identifies the tag and the use of a tamper evident tether prevents the person from removing the tag and giving it to somebody else. Hence, the code uniquely identifies the person. The tamper evident tether also prevents somebody from stealing the tag from the person. The fact that the tag uses capacitive coupling to the body is advantageous because no signal is transmitted through free space which improves privacy and security, and it also improves identification reliability because the identification is personal to the person wearing the tag. In other words, it can be more reliably determined that the person interacting with a device, such as a monitoring unit, is the person who is wearing the tag.

In exemplary embodiments, the capacitive contact comprises a conducting material, e.g. one of: copper, silver or gold.

In exemplary embodiments, the conducting material comprises a sheet of conducting material.

In exemplary embodiments, the capacitive contact comprises a composite of the conducting material and a non-conducting material, e.g. particles of metal dispersed in the non-conducting material.

In exemplary embodiments, the capacitive contact is on a body facing surface of the tether or the tag. In alternative embodiments, the capacitive contact is beneath a body facing surface of the tether or the tag.

In exemplary embodiments, the capacitive contact is covered with a layer of non-conducting material, e.g. one of: glass, plastic or polycarbonate. In exemplary embodiments, the layer of non-conducting material has a thickness of no more than 1 mm.

In exemplary embodiments, the code is represented by a modulated signal, e.g. modulated according to on-off keying. In exemplary embodiments, the modulated signal has a frequency of between 50 kHz and 300 kHz, e.g. 125 kHz.

In exemplary embodiments, the signal is coupled into the body at a regular time interval.

In exemplary embodiments, the code is encrypted.

In exemplary embodiments, the signal generator comprises an LC resonant circuit, e.g. driven by one of: a full-bridge driver; or a half-bridge driver.

In exemplary embodiments, the capacitive contact is able to receive a further signal capacitively coupled from the body of the person. In exemplary embodiments, the person identification device further comprises a mixer to convert the frequency of the further signal. In exemplary embodiments, the further signal instructs the person identification device to couple the signal into the body. In exemplary embodiments, the further signal has a frequency of between 5 MHz and 20 MHz.

In exemplary embodiments, the person identification device is powered by a battery.

According to a second aspect of the invention, there is provided a monitoring unit or detector. A capacitive contact is able to capacitively couple a signal from a body of a person. A receiver is configured to receive, from the capacitive contact, a signal representing a code. A controller is configured to determine the code from the signal. The fact that the monitoring unit uses capacitive coupling from the body is advantageous because no signal is transmitted through free space which improves privacy and security, and it also improves identification reliability because the identification is personal to the person wearing the tag. In other words, it can be reliably determined that the person interacting with the monitoring unit is the person who is wearing the tag and not merely someone who is standing nearby. The monitoring unit may be a detector which is able to detect or receive a signal capacitively coupled from a body of a person. The monitoring unit may then send the code to another device. A monitoring unit may be a device which has other functions, for example, the monitoring unit may use the code to identify the person and/or the monitoring unit may authorise the person to perform an action.

In exemplary embodiments, the controller is further configured to compare the code against a code database. In exemplary embodiments, the code database is located in either: a memory or a storage device of the monitoring unit; or a remote server with which the controller is able to communicate. In exemplary embodiments, the comparing the code against a code database determines the identity of the person. In exemplary embodiments, the controller is further configured to send the identity of the person to a monitoring centre. In exemplary embodiments, the controller is further configured to store a log of codes and the corresponding identity of the person.

In exemplary embodiments, in the event that the monitoring unit fails to determine the identity of the person, an alarm condition is triggered.

In exemplary embodiments, the monitoring unit further comprises a camera configured to capture an image or video of the person. In exemplary embodiments, the image or video of the user captured by the camera is used to verify the identity of the person.

In exemplary embodiments, the signal representing the code is represented by a modulated signal, and wherein the monitoring unit further comprises a demodulator to determine the code from the signal. In exemplary embodiments, the modulated signal is modulated according to on-off keying. In exemplary embodiments, the modulated signal has a frequency of between 50 kHz and 300 kHz, e.g. 125 kHz.

In exemplary embodiments, the monitoring unit further comprises an amplifier to amplify the signal.

In exemplary embodiments, the capacitive contact is able to capacitively couple a further signal into the body of the person. In exemplary embodiments, the further signal instructs a person identification device to couple the signal into the body. In exemplary embodiments, the further signal has a frequency of between 5 MHz and 20 MHz.

In certain embodiments, the monitoring unit is a telephone able to receive a code from the person using the telephone to make a voice call to a further person or receive a voice call from a further person, for example when monitoring a prisoner on parole. The capacitive contact may be disposed within a handset of the telephone, such that when the user holds the phone to make a voice call, a hand of the user makes contact with the capacitive contact. The advantage of using capacitive coupling with the tamper evident tether is the certainty that the person holding the phone is the person wearing the tag and the person is indentified from the signal.

In certain embodiments, the monitoring unit is a breathalyser able to receive a code from the person using the breathalyser to provide a specimen of breath. The monitoring unit may have a sample tube configured to receive the specimen of breath from the person where the sample tube forms the capacitive contact. When the person blows into the sample tube to provide the specimen of breath, the lips of the person make contact with the sample tube. The advantage of this is the certainty that the person blowing into the sample tube, and therefore providing the specimen of breath, is the person wearing the tag that is providing the code and hence the person is identified from the signal.

Optionally, the sample tube is made of plastic and the capacitive contact is formed from a conducting material disposed in the plastic material. The advantage of this is that it is cheap to manufacture, disposable and hygienic.

In certain embodiments, the monitoring unit is a key pad and the capacitive contact is disposed on the surface of the key pad. The key pad may be used to receive a PIN number, for example, from a security guard patrolling an installation who enters the PIN number into the keypad to demonstrate that the security guard has visited a location in the vicinity of the key pad. The fact that the key pad has a capacitive contact means that if the security guard is wearing a tag, the identity of the security guard that visited the location can be confirmed.

In certain embodiments, the monitoring unit is an electronic door entry and the controller uses the code to determine whether to permit access to the door.

According to a third aspect of the invention, there is provided a person identification system. The person identification system has a person identification device comprising a tag having a code, a tamper evident tether able to secure the tag to a person having a body, and a signal generator able to generate a signal representing the code. The tag has a capacitive contact able to capacitively couple the signal into the body of the person. The person identification system also has a monitoring unit comprising a capacitive contact able to capacitively couple a signal from a body of a person, a receiver configured to receive, from the capacitive contact, a signal representing a code; and a controller configured to determine the code from the signal and to compare the code against a code database.

Various embodiments of the invention will now be described, with reference to the attached figures, in which.

Figure 1:
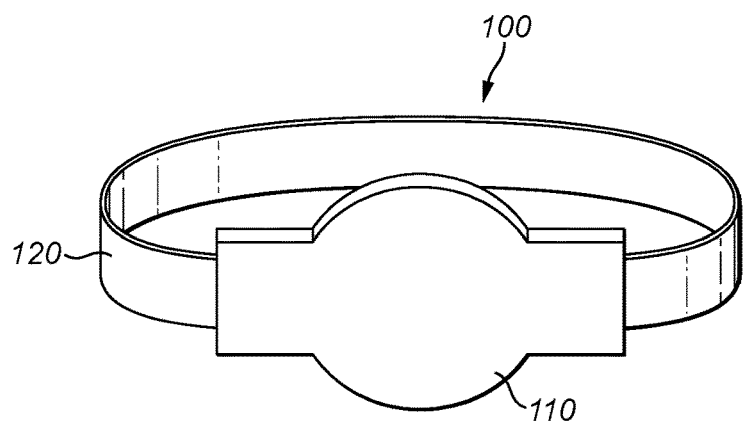
FIG. 1 is a schematic of a person identification device according to an embodiment of the first aspect of the invention.

FIG. 1 shows a person identification device 100 according to an embodiment of a first aspect of the invention. The person identification device 100 comprises a tag 110 and a tamper evident tether 120. The tamper evident tether 120 is able to secure the tag 110 to a person.

Figure 2:
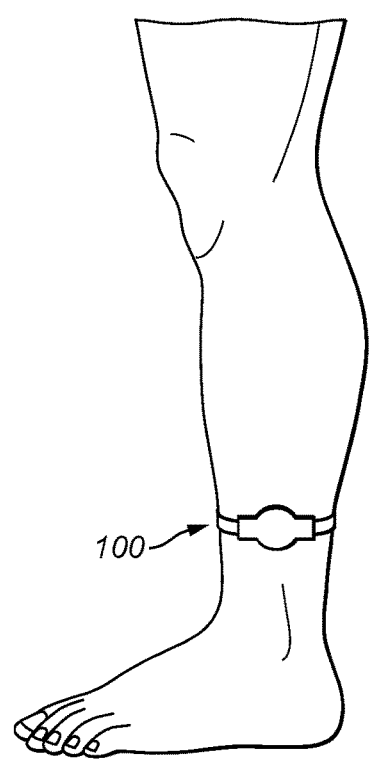
FIG. 2 shows the person identification device of FIG. 1 secured to a person.

FIG. 2 shows the person identification device 100 of FIG. 1 secured to the leg of a person. The tamper evident tether 120 could also be placed around other parts of the person, such as around an arm or a torso of the person.

The tamper evident tether 120 is secured in a way that makes the person identification device 100 difficult to remove from the person. Making the person identification device 100 difficult to remove may be achieved by making the tamper evident tether 120 from a material which is difficult to cut through or break, for example, the tamper evident tether 120 may be made from metal or a reinforced material, such as a fabric containing metal fibres, or a fabric containing Kevlar, or a fibre reinforced plastic material.

In addition, or alternatively, the tamper evident tether 120 may react to tampering. For example, the tamper evident tether 120 may contain an electrical wire, or an optical fibre, which, when cut, reports that the tamper evident tether 120 has been tampered with and may disable the person identification device 100. The tamper evident tether 120 may also contain an identifier, such as an RF-ID tag, which uniquely identifies the tamper evident tether 120, so that attempts to remove the tamper evident tether 120 and/or to replace the tamper evident tether 120 with a different tamper evident tether may be identified by the tag 110.

Person identification devices, such as those shown in FIGS. 1 and 2, are used to confirm the identity of a person, such as a security guard, or to track and monitor people, such as offenders who are on a curfew, or prisoners, or patients who are being monitored, such as an elderly or vulnerable patient. The fact that the person identification device 100 contains a tamper evident tether 120 means that the identity of the person to which the person identification device 100 is attached can be more reliably determined.

Figure 3:
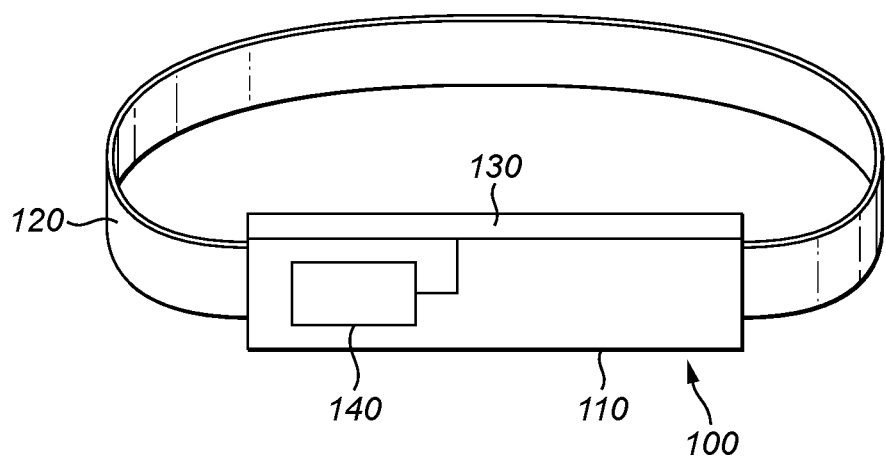
FIG. 3 shows a cross-section through the person identification device of FIG. 1 where the capacitive contact is on a body-facing surface of the tag.

FIG. 3 shows a cross section through a person identification device 100. The person identification device 100 comprises a tag 110 and a tamper evident tether 120 for securing the tag to a person. The tag 110 has a capacitive contact 130 on an external surface of the tag which, when the person identification device 100 is secured to the person, faces the body of the person.

A signal generator 140 is able to generate a signal representing a code. The signal is coupled to the capacitive contact 130 and the capacitive contact 130 capacitively couples the signal to the body of the person, so that the signal may be picked up at other locations on the body of the person.

In this embodiment, the capacitive contact is made of a sheet of conducting material, such as a metal, for example, copper, silver or gold. In general, the capacitive contact is as large as possible as this increases the signal that may be coupled into the person, although, the size of the contact may be limited by the size of the person identification device 100 which needs to be convenient for the person to wear. The capacitive contact usually has a surface area of at least 100 mm$^2$.

The person identification device 100 can be secured directly to the skin of the person, with the capacitive contact 130 in direct contact with the skin. Although typically, an air gap is allowed between the capacitive contact 130 and the skin of the person to improve the comfort for the person to whom the person identification device 100 is secured. The air gap attenuates the signal which is capacitively coupled to the body of the person, so the air gap is usually less than 10 mm to allow sufficient signal to be capacitively coupled to the body, so that the signal may be picked up at other locations on the body of the person. The strength of the signal may need to be increased to compensate for the air gap.

Alternatively, the person identification device 100 may be secured over an item of clothing worn by the person. The item of clothing will attenuate the signal, although not as badly as an air gap having the same thickness as the item of clothing.

Figure 4:
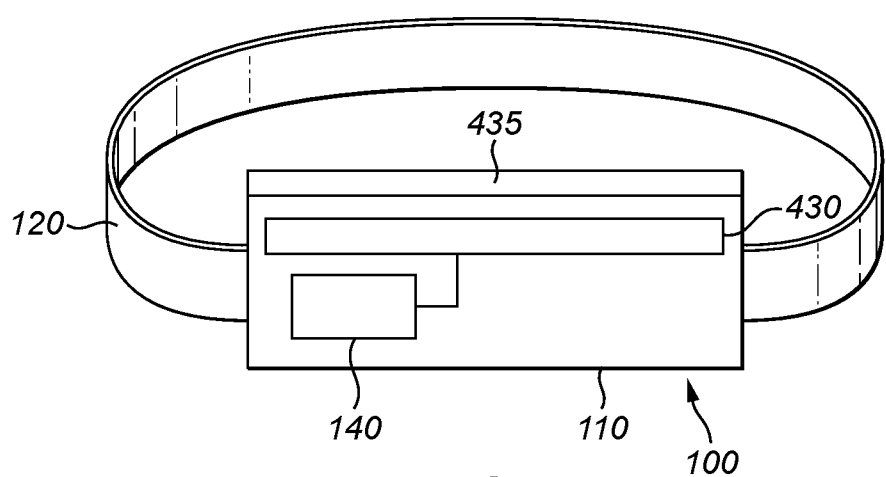
FIG. 4 shows a cross-section through the person identification device of FIG. 1 where the capacitive contact is beneath a surface of the tag.

FIG. 4 shows a cross section through an embodiment of a person identification device 100 which is similar to the person identification device of FIG. 3, except that the capacitive contact 430 is not on the external surface of the tag 110. Instead, the capacitive contact 430 in FIG. 4 is covered with a layer of non-conducing material 435.

The layer of non-conducting material 435 may be glass, plastic or polycarbonate. The layer of non-conducting material 435 will attenuate the signal slightly, so the non-conducting layer is thin enough (for example, less than 1 mm) to permit sufficient signal from the capacitive contact 430 to be capacitively coupled into the body of the person, so that the signal may be picked up at other locations on the body of the person.

Since an air gap between the capacitive contact 130 and the body tends to attenuate the amount of signal which is capacitively coupled into the body more than the presence of a non-conducting material, the person identification device 100 is formed in a way that prevents an air gap between the non-conducting layer 435 and the capacitive contact 430, for example, the capacitive contact 430 may be glued to the non-conducting later 435, or the capacitive contact 430 may be deposited or evaporated on top of the non-conducting layer 435.

Figure 5:
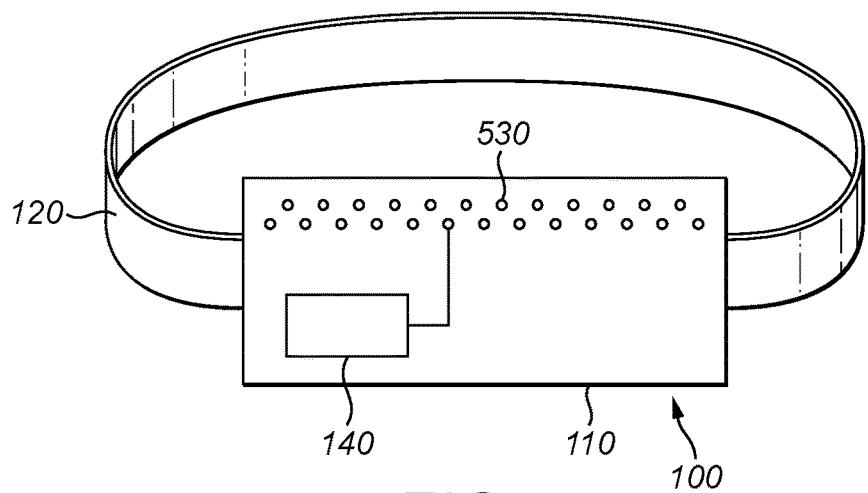
FIG. 5 shows a cross-section through the person identification device of FIG. 1 where the capacitive contact comprises a composite comprising conducting particles dispersed in a non-conducting material.

FIG. 5 shows a cross section through an embodiment of a person identification device where, unlike FIG. 3 and FIG. 4, the capacitive contact 530 is not formed of a sheet of conducting material. Instead, the capacitive contact 530 in FIG. 5 is formed from a composite of a conducting and a non-conducting material, to form a composite with conducting properties. In this case, the composite comprises particles of conducting material dispersed in the non-conducting material. The particles of conducting material may be metal particles, for example, particles of copper, silver or gold. The non-conducting material may be one of glass, plastic or polycarbonate.

The signal generator 140 shown in FIG. 3, FIG. 4 and FIG. 5 generates a signal which represents a code. The code is represented by the signal generator 140 forming a carrier signal which is modulated, for example, using an amplitude shift key modulation such as on-off keying.

Figure 6:
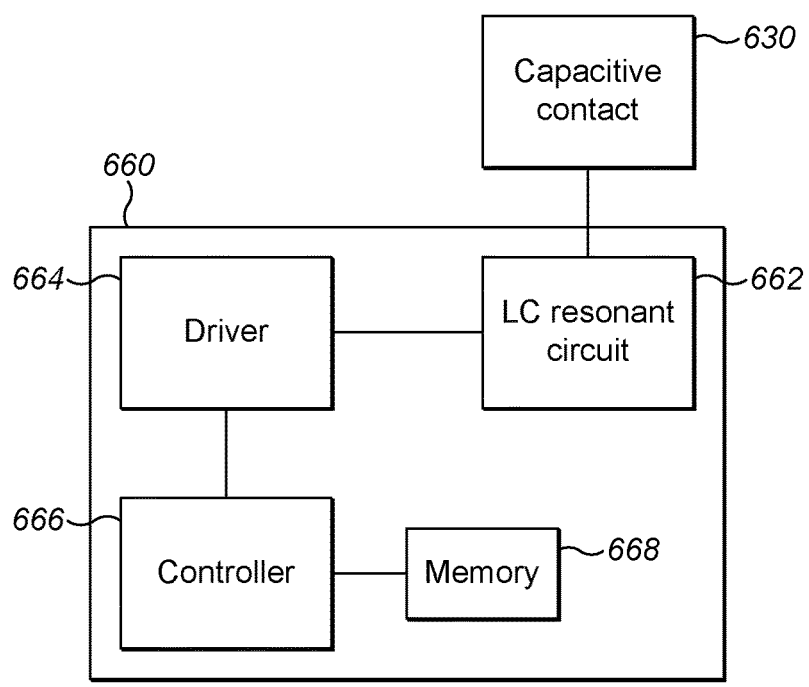
FIG. 6 shows a schematic of a circuit of a person identification device.

FIG. 6 shows a schematic of a circuit 660 which could be used to generate and couple the signal to the capacitive contact 630. The circuit 660 comprises an LC resonant circuit 662. The LC resonant circuit 662 is driven by a driver 664, such as a full bridge or a half bridge driver. A controller 666 generates the modulating signal which represents the code stored in a memory 668.

The modulated signal has a frequency towards the lower end of the radio frequency (RF) spectrum, typically between 50 kHz and 300 kHz. Using a low frequency RF signal is advantageous because it couples into the body more efficiently, thereby reducing the energy of the RF signal the person identification device 100 must generate. This is advantageous because the person identification device 100 is battery powered so reducing the energy of the RF signal improves battery life and leads to a smaller lighter device because a smaller battery may be used. In addition, the fact that a low energy RF signal is coupled into the body means that the signal cannot be detected remote from the body, thereby improving security as the code cannot be intercepted and it can be certain that the code received by a monitoring device is coming from the person touching the capacitive contact on the monitoring device and not from an external transmission.

Figure 7:
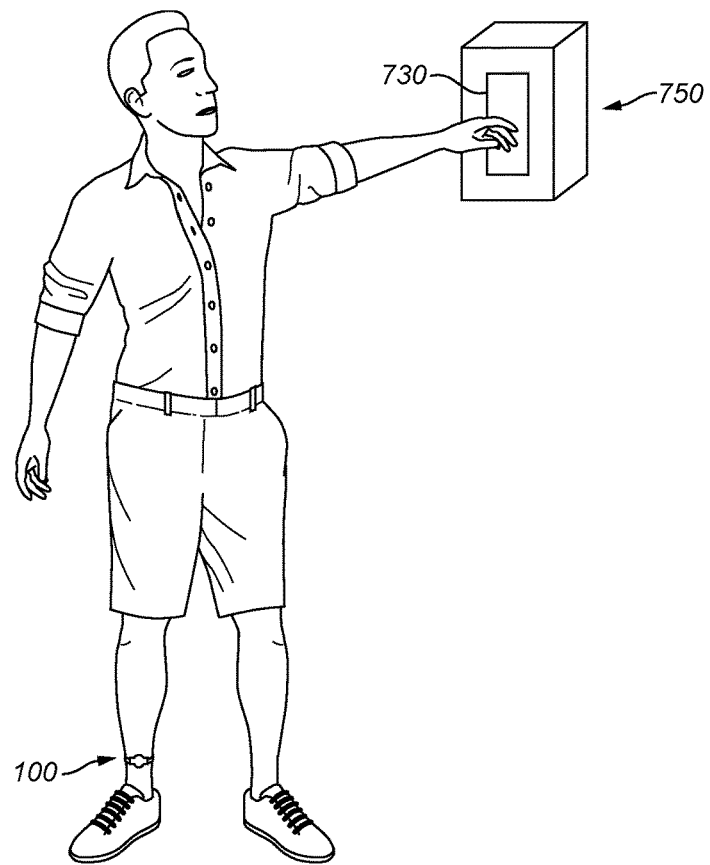
FIG. 7 shows a person interacting with a monitoring unit according to an embodiment of the second aspect of the invention.

FIG. 7 shows a person with a person identification device 100 interacting with a monitoring unit 750. The person identification device 100 couples a signal, representing a code, into the body of the person. A capacitive contact 730 on the monitoring unit 750 is able to capacitively couple a signal from the body of the person.

Figure 8:
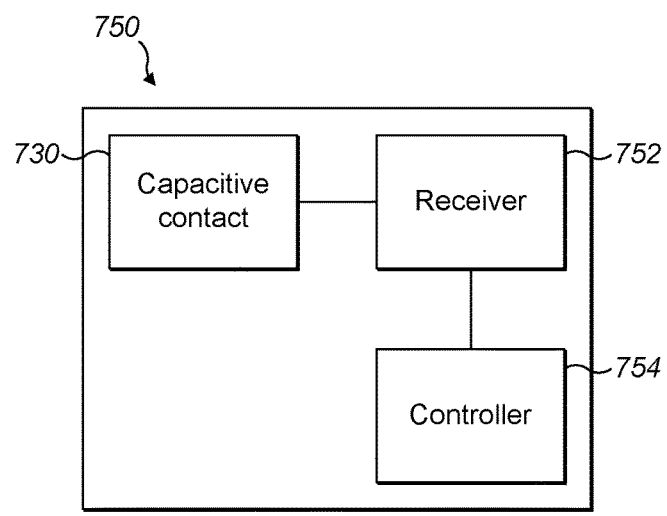
FIG. 8 shows the monitoring device in more detail.

FIG. 8 shows the monitoring unit 750 in more detail. A receiver 752 in the monitoring unit 750 receives the signal representing the code from the capacitive contact 730 and passes the signal to a controller 754 which determines the code from the signal.

Figure 9:
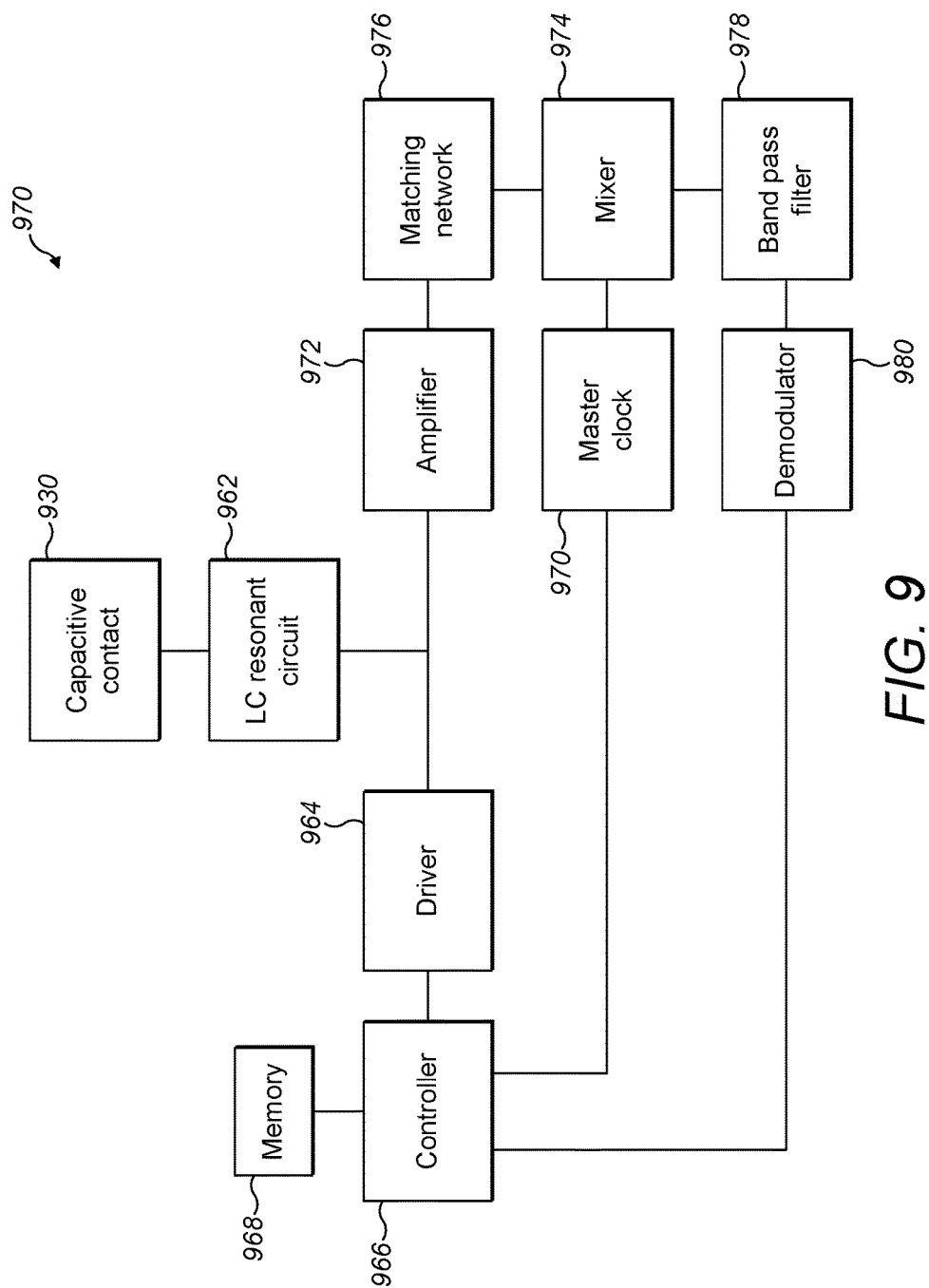
FIG. 9 shows a schematic of a circuit of the person identification device of FIG. 1 or the monitoring unit of FIG. 8.

FIG. 9 shows a schematic circuit 970 which includes the components seen in FIG. 6, which couple a signal into the body of a person, as well as additional components which permit a signal to be coupled from the body of a person.

The circuit 970 comprises a capacitive contact 930, and an LC resonant circuit 962. The LC resonant circuit 962 is driven by a driver 964, such as a full bridge or a half bridge driver. A controller 966 generates the modulating signal which represents the code stored in a memory 968.

In addition, the circuit 970 includes components which allow the circuit 970 to receive a signal capacitively coupled from the body of a person. An amplifier 972 is included to amplify the received signal which may be at a relatively low amplitude.

As mentioned previously, the person identification device 100 couples a low frequency RF signal into the body. In contrast, the monitoring unit 750 couples a high frequency signal, in the range of 5 MHz to 20 MHz, into the body because it is easier to make the tag 110 smaller if receiving at a higher frequency So, a mixer 974 is provided to down-convert the high frequency signal into a lower frequency signal that the controller 966 can handle. The mixer is attached to a master clock 970. The master clock 970 may be a clock which is incorporated in the controller 966 and therefore the frequency may be a frequency, such as 125 kHz, which is a multiple of the controller clock frequency. The output of the amplifier 972 is not impendence matched with the mixer 974, so a matching network 976 is included to transform the output impendence of the amplifier to match the input impendence of the mixer 974.

A band pass filter 978 rejects all signals other than the modulated signal. Certain embodiments use on-off keying modulation such that only the carrier of the signal needs to be passed through the band pass filter 978 which enables the band pass filter to be narrow at around or at twice the transmission baud rate, which improves noise rejection.

A demodulator 980 takes the output of the band pass filter 978 and converts it into a digital pulse train which is passed to the controller 966 to determine the code.

The circuit shown in FIG. 9 could be incorporated into a person identification device 100 to allow the person identification device 100 to both couple a signal into the body of a person, as well as to receive further signals which are capacitively coupled from the body of the person, for example, signals received from a monitoring unit 750.

The circuit shown in FIG. 9 could also be incorporated into a monitoring unit 750 to permit the monitoring unit to receive a code capacitively coupled into the body of a person wearing a person identification device 100, as well as to capacitively couple a further signal into the body of a person, such that the monitoring unit 750 may communicate with the person identification device 100. For example, the monitoring unit 750 may capacitively couple a signal into the body which instructs the person identification device 100 to capacitively couple the code into the body of the person. This means that, instead of the person identification device 100 constantly or periodically sending a signal, the person identification device 100 need only transmit the signal when it receives a further signal from the monitoring unit 750. This is an advantages because the person identification device 100 is a battery powered device and continuously or intermittently coupling the signal into the body will quickly deplete the battery of the person identification device 100. In contrast, the monitoring unit 750 is typically either a device in a fixed location which is attached to mains electricity, or else is a device where size and weight is less of an issue meaning the monitoring unit 750 may have a larger battery, so the power consumption required for the monitoring unit 750 to periodically poll for the presence of a person identification device 100 is less of an issue.

To prevent a third party from being able to determine the code that is capacitively coupled into the body of the person, the code may be encrypted. The monitoring unit 750 will poll for a person identification device 100 by capacitively coupling a response request which is encrypted with AES (advanced encryption standard) encryption. The person identification device 100 in capacitive communication with the body receives the response request and will decrypt the response request with an AES key stored in the memory 668 of the person identification device 100. The person identification device 100 will encode a response containing the code and a session key. The monitoring unit 750 will decrypt the response and authenticate the person identification device 100 based upon the session key.

The monitoring unit 750 may use the code to attempt to determine the identity of the person to whom the person identification device 100 is secured. The controller 754 in the monitoring unit 750 compares the code against a code database. The code database is located either in a memory or storage device of the monitoring unit 750, or on a remote server with which the controller 754 is able to communicate. By comparing the code against the code database, the controller attempts to determine the identity of the person to which the person identification device 100 is secured.

The controller may also send the code, or information concerning the identity of the person, to another device, for example, to permit the person wearing the tag to perform some action, such as opening a door, or authenticating a transaction.

Figure 10:
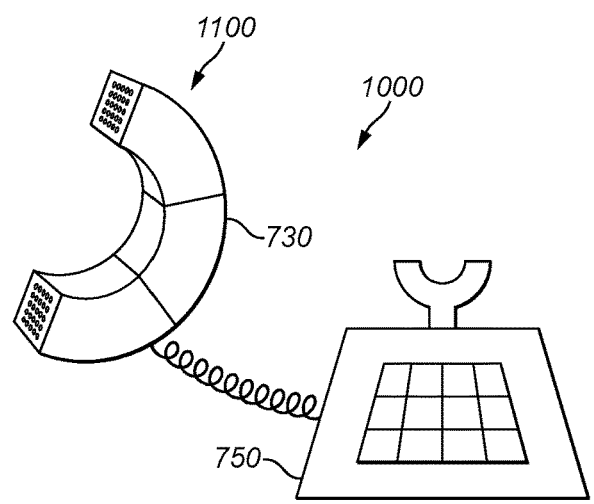
FIG. 10 shows the monitoring unit incorporated into a telephone.
Figure 11:
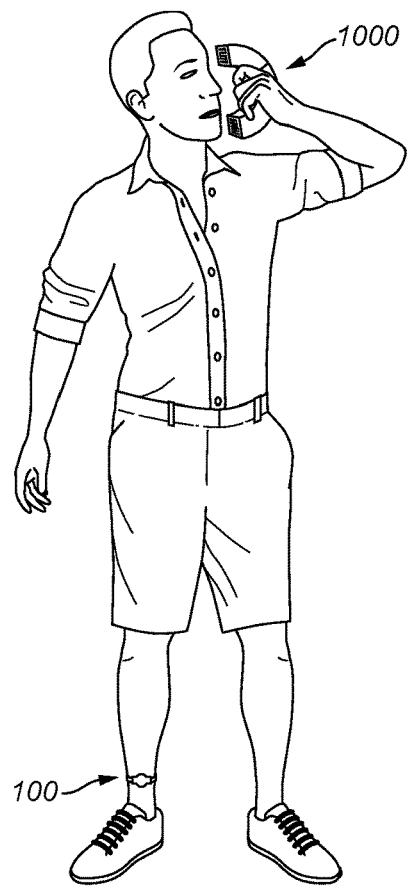
FIG. 11 shows a person using the telephone of FIG. 10.

FIG. 10 shows a monitoring unit 750 which has been incorporated into a telephone 1000. The telephone handset 1100 incorporates a capacitive contact 730, such as a sheet of conducting material, such as metal, for example, copper, silver or gold. As shown in FIG. 11, when the person to whom the person identification device 100 is secured picks up the telephone handset 1100 to make a call, the person touches the capacitive contact 730 with their hand. The person identification device 100 capacitively couples a signal containing a code into the body of the person. The signal is coupled through their body to their hand where the capacitive contact 730 capacitively couples the signal from their hand. The capacitive contact 730 sends the signal to the monitoring unit 750 which contains a circuit, such as the circuit shown in FIG. 9, which determines the code and the identity of the person. This allows the identity of the person holding the telephone handset 1100 to be identified and this information can be logged on the telephone or transmitted to a monitoring centre. The fact that the code is capacitively coupled from the person identification device 100 through the body of the person to the telephone handset 1100 means that the person to whom the person identification device 100 is secured must have been the person holding the telephone handset 1100 at the time the call was made, so that person must have been in the vicinity of the telephone. The identity of the caller may be confirmed by incorporating other identification features into the telephone 1000, for example, voice recognition or a camera to take an image of the person using the telephone 1000.

Figure 12:
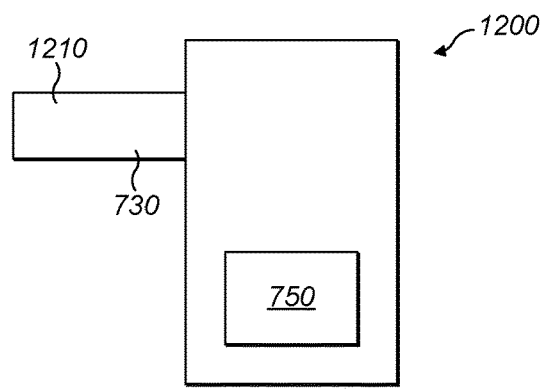
FIG. 12 shows the monitoring unit incorporated into a breathalyser.

FIG. 12 shows a monitoring unit 750 which has been incorporated into a breathalyser 1200 for determining whether a person has been consuming alcohol. The breathalyser 1200 is able to receive a code from the person who is using the breathalyser. The breathalyzer has a sample tube 1210 configured to receive the specimen of breath from the person and the sample tube 1210 comprises or forms the capacitive contact 730.

Figure 13:
FIG. 13 shows a person using the breathalyser of FIG. 12.

FIG. 13 shows a person using the breathalyser 1200. The person to whom the person identification device 100 is secured places their lips around the sample tube 1210 and blows into the sample tube 1210 to provide the specimen of breath. Since the sample tube 1210 comprises or forms the capacitive contact 730, the lips of the person make contact with the capacitive contact 730. The person identification device 100 capacitively couples a signal containing a code into the body of the person. The signal is coupled through their body to their lips where the capacitive contact 730 capacitively couples the signal from their lips. The capacitive contact 730 sends the signal to the monitoring unit 750 incorporated into the breathalyser 1200 which contains a circuit, such as the circuit shown in FIG. 9, which determines the code and determines the identity of the person. This allows the identity of the person providing the specimen of breath to be identified and this information can be logged on the breathalyser or transmitted to a monitoring centre. The fact that the code is capacitively coupled from the person identification device 100 through the body of the person to the breathalyser 1000 means that the person to whom the person identification device 100 is secured must have been the person whose lips were placed around the sample tube 1210 and therefore must be the person who provided the specimen of breath.

The sample tube 1210 may be made of plastic and may also be replaceable to improve hygiene. To form the capacitive contact 730, the plastic sample tube has particles of conducting material dispersed in the plastic material. The particles of conducting material may be metal particles, such as particles of copper, silver or gold.

In other embodiments, a monitoring unit 750 may be incorporated into other devices where it is desirable to confirm the identity of a person interacting with the device.

The monitoring unit 750 may be incorporated into an electronic door entry system and the controller uses the code to determine whether to permit access to the door.

A monitoring unit 750 may be incorporated into a key pad with the capacitive contact 730 disposed on the surface of the key pad. The key pad may be used to receive a PIN number. The fact that the key pad has a capacitive contact 730 and monitoring unit 750 means that if the person using the key pad is wearing a tag 100, the identity of the person using the key pad can be confirmed. This identity information could be used to authorise a transaction, such as at an ATM, to open or unlock a door, or to confirm that a security guard patrolling an installation has visited a particular location.

The skilled reader will understand that the capacitive contact 730 may be implemented in a number of different ways. For example, the capacitive contact 730 could be a metal plate or ring. Also, the capacitive contact 730 could be constructed from a composite material, which could also be in the form of a plate or a ring. The capacitive contact 730 could be an integral part of a device such as a phone 1000 or a breathalyser 1200 or a sample tube 1210, for example integrated with the materials forming the device. Also, the capacitive contact 730 could be in addition to the device, such as an externally fitted or retro-fit capacitive contact.

We anticipate that some uses would not need a tamper evident tether 120.

Cameras or other verification means may be used in addition to the signal.

The invention claimed is:

1. A breathalyzer comprising:
    a sample tube configured to receive a specimen of breath from a person, the sample tube comprising a capacitive contact able to capacitively couple a signal from a body of the person providing the specimen of breath, wherein the signal represents a code associated with the person using the breathalyzer to provide the specimen of breath;
    a receiver configured to receive, from the capacitive contact, the signal representing the code; and
    a controller configured to determine the code from the signal.

2. The breathalyzer claim 1, wherein the controller is further configured to compare the code against a code database for determining the identity of the person, whereby the identity of the person can be sent by the breathalyser to a monitoring center.

3. The breathalyzer of claim 2, wherein in the event that the breathalyzer fails to determine the identity of the person, an alarm condition is triggered.

4. The breathalyzer of claim 1, further comprising a camera configured to capture an image or video of the person.

5. The breathalyzer of claim 1, wherein the signal representing the code is represented by a modulated signal, and wherein the breathalyzer further comprises a demodulator to determine the code from the signal.

6. The breathalyzer of claim 1, wherein the sample tube is made of plastic and the capacitive contact is formed from a conducting material disposed in the plastic material.

7. A person identification system comprising:
    a person identification device comprising:
        a tag;
        a tamper evident tether able to secure the tag to a person who is to provide a specimen of breath, the tag having a code associated with the person;
        a signal generator able to generate a signal representing the code; and
        the tag having a first capacitive contact able to capacitively couple the signal into a body of the person; and
    a breathalyzer comprising:
        a sample tube configured to receive a specimen of breath from the person, the sample tube comprising a second capacitive contact able to capacitively couple the signal from the body of the person providing the specimen of breath, wherein the signal represents the code associated with the person using the breathalyzer to provide the specimen of breath;
        a receiver configured to receive, from the second capacitive contact, the signal representing code; and
        a controller configured to determine the code from the signal and to compare the code against a code database for the identity of the person providing the specimen of breath.

8. The person identification system of claim 7, further comprising a monitoring center, wherein the identity of the person using the breathalyzer is sent to the monitoring center.

9. The person identification system of claim 8, wherein the event that the breathalyzer fails to determine the identity of the person, an alarm condition is triggered.

* * * * *